(12) United States Patent
Won et al.

(10) Patent No.: US 12,379,320 B2
(45) Date of Patent: Aug. 5, 2025

(54) METHOD FOR ANALYZING CONTENT AND DISTRIBUTION OF BORON INTRODUCED INTO POSITIVE ELECTRODE ACTIVE MATERIAL

(71) Applicant: LG Chem, Ltd., Seoul (KR)

(72) Inventors: Jung Hye Won, Daejeon (KR); Sung Hag Kim, Daejeon (KR); Min Hwan Jung, Daejeon (KR); Jung Eun Song, Daejeon (KR); Kyeongrak Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 470 days.

(21) Appl. No.: 18/011,252

(22) PCT Filed: Sep. 1, 2021

(86) PCT No.: PCT/KR2021/011794
§ 371 (c)(1),
(2) Date: Dec. 19, 2022

(87) PCT Pub. No.: WO2022/139118
PCT Pub. Date: Jun. 30, 2022

(65) Prior Publication Data
US 2023/0324304 A1      Oct. 12, 2023

(30) Foreign Application Priority Data

Dec. 22, 2020  (KR) .................. 10-2020-0181058
Aug. 13, 2021  (KR) .................. 10-2021-0107445

(51) Int. Cl.
*G01N 1/38*    (2006.01)
*G01N 1/44*    (2006.01)
(Continued)

(52) U.S. Cl.
CPC ............... *G01N 21/73* (2013.01); *G01N 1/38* (2013.01); *G01N 1/44* (2013.01); *G01N 33/2022* (2019.01)

(58) Field of Classification Search
CPC   G01N 21/73; G01N 1/38; G01N 1/44; G01N 33/2022; C01P 2002/54;
(Continued)

(56) References Cited

U.S. PATENT DOCUMENTS

2012/0177994 A1\*  7/2012  Kim ...................... C01G 51/20
                                                    252/182.1
2013/0089787 A1    4/2013  Nagai
(Continued)

FOREIGN PATENT DOCUMENTS

CN    104155267 A    11/2014
CN    104949961 B    11/2017
(Continued)

OTHER PUBLICATIONS

Kook et al "Positive Active Material for Lithium Secondary Battery, Preparing Method Thereof, and Lithium Secondary Battery Comprising Positive Electrode Including Positive Active Material", Jan. 20, 2021 (Year: 2021).\*

(Continued)

*Primary Examiner* — Sang H Nguyen
(74) *Attorney, Agent, or Firm* — Lerner David LLP

(57) ABSTRACT

A method for analyzing the content of boron in a cathode active material is disclosed herein. In some embodiments, a method comprises (S1) introducing boron into a cathode active material to prepare a cathode active material sample, (S2) separating a first liquid layer and a first precipitate by dissolving the sample in water, treating the first liquid layer with acid to form a first resulting solution, and measuring the boron concentration in the first resulting solution by induc- (Continued)

tively coupled plasma optical emission spectroscopy (ICP-OES), (S3) separating a second liquid layer and a second precipitate by dissolving the first precipitate in water, treating the second liquid layer with acid to form a second resulting solution, and measuring the boron concentration of the second resulting solution by ICP-OES, and (S4) measuring the boron concentration of a third resulting solution, obtained by adding acid and hydrogen peroxide to the second precipitate, by ICP-OES.

9 Claims, 1 Drawing Sheet

(51) Int. Cl.
   *G01N 21/73* (2006.01)
   *G01N 33/2022* (2019.01)
(58) Field of Classification Search
   CPC ........ C01G 53/50; Y02E 60/10; H01M 4/366; H01M 4/62; H01M 4/525; H01M 10/052
   See application file for complete search history.

(56) References Cited

U.S. PATENT DOCUMENTS

| | | | |
|---|---|---|---|
| 2013/0316239 A1* | 11/2013 | Okamoto | C01G 53/50 |
| | | | 429/223 |
| 2015/0147630 A1 | 5/2015 | Nakano et al. | |
| 2016/0013476 A1 | 1/2016 | Oh et al. | |
| 2018/0131006 A1 | 5/2018 | Kokubu et al. | |
| 2018/0212237 A1* | 7/2018 | Lee | C01G 53/42 |
| 2018/0261835 A1 | 9/2018 | Ogata et al. | |
| 2019/0173076 A1* | 6/2019 | Kim | H01M 4/525 |
| 2019/0312279 A1 | 10/2019 | Otsuka et al. | |
| 2020/0127287 A1 | 4/2020 | Yamauchi et al. | |
| 2020/0185709 A1* | 6/2020 | Zhou | H01M 4/04 |
| 2020/0358094 A1* | 11/2020 | Oshita | H01M 10/0525 |
| 2021/0013509 A1 | 1/2021 | Otsuka et al. | |
| 2022/0246911 A1 | 8/2022 | Goshima et al. | |

FOREIGN PATENT DOCUMENTS

| | | |
|---|---|---|
| JP | 2004325380 A | 11/2004 |
| JP | 2013243091 A | 12/2013 |
| JP | 2018036081 A | 3/2018 |
| JP | 2018045802 A | 3/2018 |
| JP | 6685002 B2 | 4/2020 |
| KR | 20120081808 A | 7/2012 |
| KR | 20150050458 A | 5/2015 |
| KR | 20160149450 A | 12/2016 |
| KR | 20190011945 A | 2/2019 |
| KR | 20200042224 A | 4/2020 |
| WO | 2011162178 A1 | 12/2011 |
| WO | 2019039567 A1 | 2/2019 |
| WO | 2019182064 A1 | 9/2019 |
| WO | 2020230424 A1 | 11/2020 |

OTHER PUBLICATIONS

Extended European Search Report including Written Opinion for Application No. 21911187.9 dated Nov. 3, 2023, pp. 1-8.
International Search Report for Application No. PCT/KR2021/011794 mailed Dec. 16, 2021, 2 pages.
Puranen, A. et al., "Lithium and boron analysis by LA-ICP-MS results from a bowed PWR rod with contact," EPJ Nuclear Sci. Technol., vol. 3, No. 2, Dec. 7, 2016, pp. 1-9, EDP Sciences (2017).

* cited by examiner

[Fig. 1]
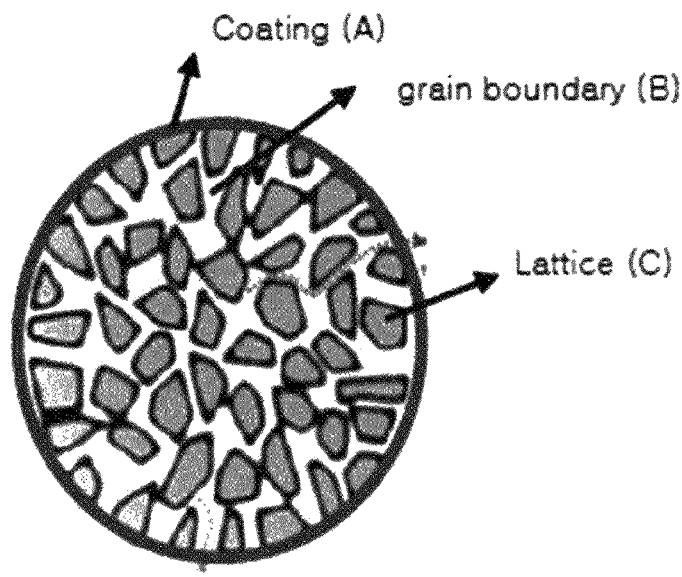
[Fig. 2]
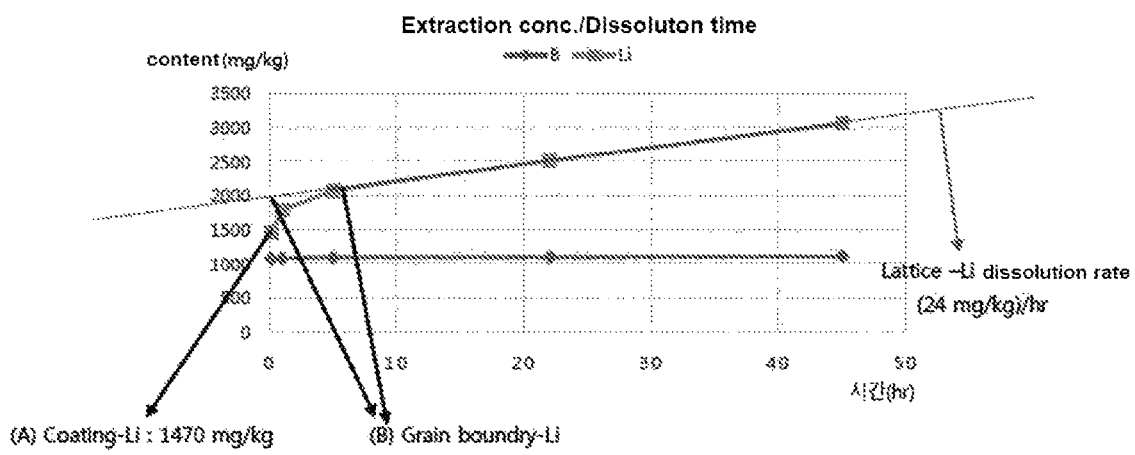

METHOD FOR ANALYZING CONTENT AND DISTRIBUTION OF BORON INTRODUCED INTO POSITIVE ELECTRODE ACTIVE MATERIAL

CROSS-REFERENCE TO RELATED APPLICATIONS

This application is a national phase entry under 35 U.S.C. § 371 of International Application No. PCT/KR2021/011794, filed on Sep. 1, 2021, which claims benefit of priority from Korean Patent Application No. 10-2020-0181058, filed on Dec. 22, 2020 and Korean Patent Application No. 10-2021-0107445, filed on Aug. 13, 2021, the disclosures of which are incorporated by reference herein.

TECHNICAL FIELD

The present invention relates to an analysis method of distribution pattern and content for each distribution position of boron introduced into a cathode active material for a lithium secondary battery.

BACKGROUND ART

Lithium secondary batteries generally have a structure including an electrode assembly composed of a cathode and an anode comprising electrode active materials capable of intercalating/releasing lithium ions and a separator interposed between the two electrodes, and an electrolyte solution which is a transfer medium for lithium ions. Lithium ions move between the anode and the cathode through the electrolyte, causing charging and discharging of batteries.

The secondary batteries undergo problems such as deterioration of life characteristics, decomposition of electrolytes or deterioration of active materials during repeated charging and discharging procedures. In addition, when impurities are present on the surfaces of the active materials during the manufacture of electrodes of secondary batteries, the batteries are subject to swelling due to the reaction between impurities and the electrolyte and change over time.

In order to overcome the above problems, the electrode active material may be coated or doped with various materials. For example, when lithium transition metal oxides such as lithium-nickel-manganese-cobalt-based oxides are used as the cathode active material, coating or doping with boron results in formation of oxygen-sealing structures, thereby capacity reduction can be slowed down. In addition, boron contained in the cathode active material may enhance structural stability by strengthening the bonding between transition metals and oxygen. In general, the introduction of boron into the cathode active material is carried out by mixing the cathode active material and boric acid ($H_3BO_3$) and firing at a high temperature wherein boron may penetrate to the inside of the cathode active material or may remain in the form of Li—B—O compound on the surface and outside thereof.

In order to evaluate effect of boron on performance of a cathode active material, it is important to understand distribution pattern of boron inside and outside the active material, and in particular, to measure content of boron penetrating to the inside. The current method for analyzing components of a cathode active material is to perform measurement by inductively coupled plasma optical emission spectroscopy (ICP-OES) after pretreatment with acid. In this method, it is possible to quantify even the boron that has penetrated to the inside of primary grains of the structurally stable cathode active material by using acid.

However, a technique for separately analyzing boron inside and outside of the cathode active material has not yet been developed.

DETAILED DESCRIPTION OF THE INVENTION

Technical Problem

Accordingly, an object of the present invention is to provide an analysis method of content for each distribution position of boron introduced to improve performance of a cathode active material used in a lithium secondary battery.

Solution to Problem

According to one aspect of the invention, there is provided an analysis method of content of boron introduced into a cathode active material, the method comprising:

(S1) introducing boron into a cathode active material to prepare a cathode active material sample;

(S2) dissolving the cathode active material sample in water to obtain a first liquid layer and a first precipitate, treating the first liquid layer with acid to form a first resulting solution, and then determining the concentration of boron in the first resulting solution by inductively coupled plasma optical emission spectroscopy (ICP-OES);

(S3) dissolving the first precipitate in water to obtain a second liquid layer and a second precipitate, treating the second liquid layer with acid to from a second resulting solution, and determining the concentration of boron in the second resulting solution by ICP-OES; and (S4) adding acid and hydrogen peroxide to the second precipitate to form a third resulting solution, and determining the concentration of boron in the third resulting solution by ICP-OES.

In addition, the present invention provides a cathode active material for a secondary battery of which boron content is determined by the above analysis method, wherein boron is introduced into a lithium transition metal oxide such that boron is present at least one of on the surface, at grain boundary, or in lattice of the lithium transition metal oxide particles.

Effect of the Invention

According to the present invention, it is possible to sequentially extract and analyze boron introduced to improve performance of a cathode active material for a lithium secondary battery by using a difference in solubility in water and an acid according to the distribution position of boron, thereby determining the optimal content of boron required for improving performance of the cathode active material through the distribution pattern of boron in the cathode active material.

BRIEF DESCRIPTION OF DRAWINGS

FIG. 1 illustrates a distribution pattern of boron introduced to the cathode active material.

FIG. 2 shows the extraction results of boron and lithium according to the dissolution time in water of the cathode active material sample in the analysis process according to the embodiment.

BEST MODE FOR CARRYING OUT THE INVENTION

Hereinafter, the terms or words used in the present specification and claims should not be construed as being limited to conventional or dictionary meanings, and should be interpreted as meanings and concepts consistent with the technical spirit of the present invention based on principles that the inventor can appropriately define the concept of a term to best describe his invention.

In addition, the configuration shown in the embodiments and drawings described in this specification is only the most preferred embodiment of the present invention and does not represent all of the technical idea of the present invention, so it should be understood that various equivalents and modifications may be substituted for them at the time of filing the present application.

One embodiment of the present invention relates to an analysis method of content of boron introduced to improve the performance of a cathode active material for a lithium secondary battery according to a distribution position. Hereinafter, the method will be described in detail for each step.

First, a cathode active material sample into which boron is introduced is prepared (S1).

Specifically, the cathode active material sample may be prepared by dry mixing a boron-containing compound and a cathode active material, followed by firing at a high temperature.

The boron-containing compound may comprise at least one compound selected from the group consisting of $HaBO_3$, $B_2O_3$, $C_6H_5B(OH)_2$, $(C_6H_5O)_3B$, $[CH_3(CH_2)_3O]_3B$, $C_{13}H_{19}BO_3$, $C_3H_9B_3O_6$, and $(C_3H_7O)_3B$.

The cathode active material may comprise a lithium transition metal oxide represented by the following formula 1.

$$Li[Ni_xMn_yCo_zM_v]O_2 \qquad \text{[Formula 1]}$$

In the formula, M is one or two or more selected from the group consisting of Al, Zr, Zn, Ti, Mg, Ga and In; $0 \leq x \leq 1.0$, $0 \leq y \leq 0.6$, $0 \leq z \leq 0.6$ and $0 \leq v \leq 0.1$.

In addition, the firing may be carried out near the melting point of the boron-containing compound, for example at 130° C. to 300° C., such as 130° C. to 200° C., for 3 hours to 10 hours. When the firing temperature satisfies the above temperature range, the boron-containing compound is sufficiently melted and non-uniform reaction due to excessive temperature can be prevented.

After the firing process, boron may be coated on the surface of the cathode active material or penetrate to the inside of the cathode active material to be distributed between primary grains or secondary grains. Referring to FIG. 1, boron is introduced into the cathode active material such that it exists in the coating layer on the surface (A), at grain boundary (B), and/or in lattice (C) to form lithium boron oxides such as $LiBO_2$, $LiB_4O_7$, etc.

The solubility of boron in water may vary depending on the distribution position of the boron in the cathode active material. For example, boron present in the coating layer (A) of the cathode active material is readily dissolved in water, while boron present at grain boundary (B) is dissolved in water over a long period of time and boron doped in lattice (C) is hardly dissolved in water and can be dissolved through acid treatment. Therefore, in the present invention, boron present in the cathode active material sample is sequentially extracted by using the difference in solubility for each distribution position.

In particular, the cathode active material sample is dissolved in water to obtain a first liquid layer and a first insoluble precipitate, and then the first liquid layer is treated with acid (S2). At this time, dissolving the sample in water may be performed at room temperature for 1 to 10 minutes.

The first liquid layer is a result of rapidly dissolving boron coated on the surface of the cathode active material in water, and thus the first liquid layer is subjected to acid treatment to induce dissolution of remaining boron. In addition, through the acid treatment, acid concentration and solution viscosity can be maintained as same level as in the single extraction of boron.

The acid-treated solution of the first liquid layer may be analyzed by inductively coupled plasma optical emission spectroscopy (ICP-OES) to measure the boron concentration. The ICP-OES may be performed in a conventional manner in the art, for example, under the condition as exemplified in the following Example. The content (A) of boron coated on the surface of the cathode active material may be calculated using the boron concentration as measured above.

Then, to extract boron present at grain boundary of the cathode active material sample, the first precipitate is dissolved in water to obtain a second liquid layer and a second insoluble precipitate, and then the second liquid layer is treated with acid (S3). At this time, dissolving the first precipitate in water may be performed at room temperature for 1 to 10 hours.

The acid-treated solution of the second liquid layer may be analyzed by ICP-OES to measure the boron concentration, and the content (B) of boron present at grain boundary of the cathode active material may be calculated using the boron concentration as measured above.

Then, to extract boron doped in lattice of the cathode active material sample, the second precipitate is dissolved by adding acid and hydrogen peroxide (S4). At this time, dissolving the second precipitate may be performed for 1 to 5 hours.

The solution obtained by treating the second precipitate with acid and hydrogen peroxide is analyzed by ICP-OES to measure the boron concentration, and the content (C) of boron doped in lattice of the cathode active material may be calculated using the boron concentration as measured above.

The content (C) of boron doped in lattice of the active material particles which is determined through extraction and ICP-OES analysis in a sequential process corresponds to a value according to Equation 1 below:

Boron content in lattice (C)=Total boron content in the sample (D)−(Boron content in the coating layer (A)+Boron content at grain boundary (B))  [Equation 1]

In the steps of extracting boron for each distribution position, the acid that may be used for the first liquid layer, the second liquid layer and the second precipitate may be hydrochloric acid, and the acid may be used in an amount of 0.01 to 10 ml, preferably 5 to 10 ml based on 1 g of each object to be treated.

Meanwhile, the hydrogen peroxide is used to extract remaining boron that has not been dissolved by the acid, and the acid and hydrogen peroxide may be used in a volume ratio of 1:0.3 to 1:0.7, for example, 1:0.5.

As described above, when boron introduced into the cathode active material is sequentially extracted and analyzed by using a difference in solubility in water and an acid, it is possible to quantify the amount of boron present in each position according to the distribution pattern of boron in the cathode active material, thereby identifying the correlation between the performance improvement and the amount of boron introduced. From this, it can be confirmed that the optimal content of boron that contributes to the performance improvement of the cathode material.

Accordingly, the present invention further provides a cathode active material for a secondary battery of which boron content is determined by the above analysis method, wherein boron is introduced into lithium transition metal oxide particles such that boron is present at least one of on the surface, at grain boundary, and in lattice of the lithium transition metal oxide particles.

In the cathode active material according to the present invention, based on the total amount of boron introduced, 80 to 100% of boron may be present on the surface, 0 to 1% of boron may be present at grain boundary, and 0 to 20% of boron may be present in lattice of the lithium transition metal oxide particles.

MODE FOR CARRYING OUT THE INVENTION

Hereinafter, examples will be described in detail for helping understanding of the present invention. However, the examples according to the present invention may be modified in various other forms, and the scope of the present invention should not be construed as being limited to the following embodiments. The embodiments of the present invention are provided for more complete explanation of the present invention to those of ordinary skill in the art.

Example 1: Extraction and Content Analysis According to Distribution Position of Boron Introduced into Cathode Active Material (Step 1) Preparation of Cathode Active Material Sample $LiNi_{0.78}Mn_{0.11}Co_{0.11}O_2$ as a cathode active material and $H_3BO_3$ as a boron-containing compound were mixed in a dry mixer (CYCLOMIX, HOSOKAWA Micron Corporation), and then the resulting powders were fired at 150° C. for 5 hours. Through this process, three samples with boron introduced into the cathode active material were obtained, wherein the cathode active material and the boron-containing compound are applied to the sample in an amount as shown in Table 1, respectively.

(Step 2) Extraction and Content Measurement of Boron Present in Coating Layer of Cathode Active Material 0.1 g of each of the three samples obtained in step 1 was aliquoted and put into a vial, and it was dissolved by adding 20 g of ultrapure water thereto and then shaking at room temperature for 5 minutes. The resulting solution was allowed to stand so that a first liquid layer and a first precipitate (insoluble) were separated, and then filtered through a 0.45 μm filter.

After filtration, 0.5 ml of concentrated hydrochloric acid and 0.1 ml of an internal standard solution (Sc 1000 μg/ml) were added to 10 g of the first liquid layer, and the resulting solution was analyzed by ICP-OES. At this time, the ICP-OES (AVIO500, Perkin Elmer) was operated with the following conditions: Forward Power 1300 W; Torch Height 15 mm; Plasma gas flow rate 15.00 L/min; Sample gas flow rate 0.8 L/min; Auxiliary gas flow rate 0.20 L/min and Pump speed 1.5 ml/m.

From the concentration of boron measured by the ICP-OES, the content (A) of boron present in the coating layer of the cathode active material was calculated.

(Step 3) Extraction and Content Measurement of Boron Present at Grain Boundary of Cathode Active Material 0.1 g of the first precipitates (insoluble) separated in step 2 were put into a vial and dissolved by adding 20 g of ultrapure water thereto and then shaking at room temperature for 5 hours. The resulting solution was allowed to stand so that a second liquid layer and a second precipitate (insoluble) were separated, and then filtered through a 0.45 μm filter.

After filtration, 0.5 ml of concentrated hydrochloric acid and 0.1 ml of an internal standard solution (Sc 1000 μg/ml) were added to 10 g of the second liquid layer, and the resulting solution was analyzed by ICP-OES under the same conditions as in step 2.

From the concentration of boron measured by the ICP-OES, the content (B) of boron present at grain boundary of the cathode active material was calculated.

(Step 4) Extraction and Content Measurement of Boron in Lattice of Cathode Active Material 0.1 g of the second precipitates (insoluble) separated in step 3 were put into a vial and dissolved by adding 1 ml of concentrated hydrochloric acid and 0.5 ml of hydrogen peroxide at room temperature for 3 hours, and bubbles and heat were generated during the dissolution process.

0.1 ml of an internal standard solution (Sc 1000 μg/ml) was added to the resulting solution, and ICP-OES analysis was performed under the same conditions as in step 2.

From the concentration of boron measured by the ICP-OES, the content (C) of boron in lattice of the cathode active material was calculated.

Comparative Example 1: Single Extraction and Content Analysis of Boron Introduced into Cathode Active Material 0.1 g of each of the three samples obtained in step 1 of Example was aliquoted and put into a vial, and it was dissolved by adding 1 ml of concentrated hydrochloric acid and 0.5 ml of hydrogen peroxide at room temperature for 3 hours, and bubbles and heat were generated during the dissolution process.

0.1 ml of an internal standard solution (Sc 1000 μg/ml) was added to the resulting solution, and ICP-OES analysis was performed under the same conditions as in step 2.

From the concentration of boron measured by the ICP-OES, the content (D) of boron introduced into the cathode active material was calculated.

The analysis results according to Example and Comparative Example are shown in Table 1 below.

TABLE 1

| | Boron content (mg/kg of cathode active material) | Sample 1 | Sample 2 | Sample 3 |
|---|---|---|---|---|
| | Amount used in sample preparation | 1000 | 1000 | 1000 |
| Example 1 | Coating boron (A) | 1035 | 420 | 540 |
| | Boundary boron (B) | <10 | <10 | <10 |
| | Lattice boron (C) | <10 | 45 | 125 |
| Comparative Example 1 | Total boron (D) | 1035 | 465 | 665 |

From Table 1, even if the amount of boron used in preparing the sample was the same, the content of the coated or doped boron in each sample was different depending on reactivity between boron and the active material (especially, for Sample 1, it was found that the content in the active material was different from the amount of boron introduced due to the weight error when weighing boron raw materials or the purity of boron). By sequentially extracting boron using the difference in solubility in water and an acid according to the distribution position in the active material, the content of boron to penetrate to the inside could be measured. That is, it can be seen that, in Sample 1, most of the boron introduced into the cathode active material is present in the coating layer (A) on the surface, and in Samples 2 and 3, the introduced boron is dispersed and distributed in the coating layer (A), at grain boundary (B) and in lattice (C). Through the distribution pattern of boron, it is possible to determine the optimal content of boron required to improve the performance of the cathode active material.

In addition, from the results of Comparative Example, it was confirmed that the content (C) of boron in lattice of the cathode active material particles corresponds to a value according to Equation 1 below.

Boron content in lattice (C)=Total boron content in the sample (D)−(Boron content in the coating layer (A)+Boron content at grain boundary (B))   [Equation 1]

Therefore, as in Example 1, when boron introduced into the cathode active material is extracted and analyzed according to the distribution position, it is possible to quantify the amount of boron present in each position according to the distribution pattern of boron in the cathode active material, thereby identifying correlation between the performance improvement and the amount of boron introduced. From this, it can be determined the optimal content of boron that contributes to the performance improvement of the cathode material.

Example 2

In order to determine extraction content of boron and lithium according to the dissolution time in water of the cathode active material into which boron is introduced, $LiNi_{0.78}Mn_{0.11}Co_{0.11}O_2$ and $H_3BO_3$ were dry mixed and fired as in Step 1 of Example 1 to produce a sample (1000 mg of boron/1 kg of cathode active material), and then 0.1 g of the sample was aliquoted and put into a vial and it was dissolved by adding 20 g of ultrapure water thereto at room temperature, and ICP-OES analysis was performed under the same conditions as in Example 1 depending on the dissolution time.

As a result, the contents of boron and lithium depending on the dissolution time are shown in Table 2 and FIG. 2.

TABLE 2

| Dissolution time (hr) | Content (mg/1 kg of cathode active material) | | Li dissolution rate (corresponds to the straight line slope of FIG. 2) |
|---|---|---|---|
| | B | Li | |
| 0.1 | 1068 | 1470 | |
| 1 | 1084 | 1786 | 314 |
| 5 | 1093 | 2076 | 72 |
| 22 | 1093 | 2511 | 25.6 |
| 45 | 1105 | 3052 | 23.5 |

From Table 2 and FIG. 2, the content (extraction concentration) of boron is not significantly changed according to the dissolution time and most of boron is present in the coating, while the slope of the content (extraction concentration) of lithium is divided into three stages according to the dissolution time and the lithium results are similar to the results for Samples 2 and 3 used in Example 1. These results will be used as indirect evidence that the lithium applied to the cathode active material at a high concentration has different distribution pattern in the active material particles depending on the dissolution rate. The difference in the dissolution rate of the lithium component is presumed to be due to partial desorption and dissolution of lithium from the structure of the NCM-based cathode active material (Li[Ni/Co/Mn]$O_2$).

The invention claimed is:

1. An analysis method of content of boron introduced into a cathode active material, the method comprising:
   (S1) introducing boron into a cathode active material to prepare a cathode active material sample;
   (S2) dissolving the cathode active material sample in water to obtain a first liquid layer and a first precipitate, treating the first liquid layer with acid to form a first resulting solution, and then determining a concentration of boron in the first resulting solution by inductively coupled plasma optical emission spectroscopy (ICP-OES);
   (S3) dissolving the first precipitate in water to obtain a second liquid layer and a second precipitate, treating the second liquid layer with acid to form a second resulting solution, and then determining a concentration of boron in the second resulting solution by ICP-OES; and
   (S4) adding acid and hydrogen peroxide to the second precipitate to form a third resulting solution, and then determining a concentration of boron in the third resulting solution by ICP-OES.

2. The analysis method according to claim 1, wherein step S1 comprises:
   dry mixing a boron-containing compound and the cathode active material; and
   firing the dry mixture, such that boron is present at least one of on the surface, at grain boundary, or in lattice of the cathode active material particles to form the cathode active material sample.

3. The analysis method according to claim 2, wherein the boron-containing compound comprises at least one compound selected from the group consisting of $H_3BO_3$, $B_2O_3$, $C_6H_5B(OH)_2$, $(C_6H_5O)_3B$, $[CH_3(CH_2)_3O]_3B$, $C_{13}H_{19}BO_3$, $C_3H_9B_3O_6$, and $(C_3H_7O)_3B$.

4. The analysis method according to claim 2, wherein the cathode active material comprises a lithium transition metal oxide represented by the following formula 1:

$Li[Ni_xMn_yCo_zM_v]O_2$   [Formula 1]

wherein M is one or two or more selected from the group consisting of Al, Zr, Zn, Ti, Mg, Ga and In;
$0 \leq x \leq 1.0$,
$0 \leq y \leq 0.6$,
$0 \leq z \leq 0.6$, and
$0 \leq v \leq 0.1$.

5. The analysis method according to claim 2, wherein the firing is dry mixture is fired at a temperature of 130° C. to 300° C.

6. The analysis method according to claim 1, wherein the amount of the acid used in the steps S2 to S4 is a range of 0.01 to 10 ml based on 1 g of the object to be treated.

7. The analysis method according to claim 1, wherein the acid used in the steps S2 to S4 comprises hydrochloric acid.

8. The analysis method according to claim 1, wherein the method comprising:
- calculating a content (A) of boron coated on the surface of the cathode active material using the boron concentration measured in step S2,
- calculating a content (B) of boron present at a grain boundary of the cathode active material using the boron concentration measured in step S3, and
- calculating a content (C) of boron doped in a lattice of the cathode active material using the boron concentration measured in step S4.

9. The analysis method according to claim 8, wherein the content (C) of boron present in the lattice of the cathode active material is determined according to Equation 1 below:

$$\text{Boron content in lattice (C)} = \text{Total boron content in the sample (D)} - (\text{Boron content in the coating layer (A)} + \text{Boron content at grain boundary (B)}) \quad [\text{Equation 1}].$$

* * * * *